United States Patent [19]

Hertel et al.

[11] Patent Number: 4,983,724

[45] Date of Patent: Jan. 8, 1991

[54] INVERSION OF 2,2-DIFLUORORIBOSE TO A 2,2-DIFLUOROXYLOSE AND INTERMEDIATES THEREFOR

[75] Inventors: Larry W. Hertel; Marie T. Reamer, both of Indianapolis, Ind.

[73] Assignee: Eli Lilly and Company, Indianapolis, Ind.

[21] Appl. No.: 394,394

[22] Filed: Aug. 15, 1989

Related U.S. Application Data

[63] Continuation-in-part of Ser. No. 295,321, Jan. 11, 1989, abandoned, which is a continuation-in-part of Ser. No. 156,116, Feb. 16, 1988, abandoned.

[51] Int. Cl.$^5$ .............................................. C07H 1/00
[52] U.S. Cl. .................................... 536/4.1; 536/17.1; 536/122
[58] Field of Search ........................... 536/23, 29, 4.1

[56] References Cited

U.S. PATENT DOCUMENTS 4,526,988  7/1985  Hertel ................................. 536/23
4,692,434  9/1987  Hertel ................................. 536/23

OTHER PUBLICATIONS

A. F. Cook et al. "Carbodiimide–Sulfoxide Reactions, VI Syntheses of 2'- and 3'-Ketouridines", *Journal of American Chem. Soc.*, 89(11), pp. 2697–2705, (1967).

K. Onodera et al., "Oxidation of Carbohydrates . . . Pentaoxide", *Carbohydrate Research* 6, pp. 276–285, (1968).

L. Hertel et al., *Synthesis of 2,3-dideoxy-2,2-difluoro-D-ribofuranosylnucleosides,* Gordon Conference, Jul. 10, 1989.

J. S. Brimacombe, *Angewandte Chemie, Int. Ed. Engl.,* 8(6), 401–409, (1969).

*Primary Examiner*—Christine Nucker
*Assistant Examiner*—James O. Wilson
*Attorney, Agent, or Firm*—Douglas J. Taylor; Leroy Whitaker

[57] ABSTRACT

A process and intermediates useful for the invrsion of 2-deoxy-2,2-difluororibose analogs to provide 2-deoxy-2,2-difluoroxylose analogs is described.

18 Claims, No Drawings

INVERSION OF 2,2-DIFLUORORIBOSE TO A 2,2-DIFLUOROXYLOSE AND INTERMEDIATES THEREFOR

CROSS REFERENCE

This application is a continuation-in-part of copending application Ser. No. 07/295,321, now abandoned (July 6, 1990), filed Jan. 11, 1989, which is a continuation-in-part of copending application Ser. No. 07/156,116, filed Feb. 16, 1988, now abandoned.

BACKGROUND OF THE INVENTION

While the treatment of cancer was once considered impossible, great strides have been made during the past ten years in controlling the ravages of this often fatal disease. Several drugs which contribute to the increasing survival rate of patients diagnosed as having one of several types of cancer are now routinely used clinically. The most commonly employed antitumor drugs include methotrexate, doxorubicin, cytarabine and the vinca alkaloids such as vincristine. However, research continues to develop more effective compounds with improved efficacy and greater safety for subjects under treatment for cancer.

The search for chemical compounds with oncolytic activity has revealed a class of 2'-deoxy-2',2'-difluoronucleosides which exhibit excellent activity against a variety of tumors, both solid and non-solid types, as disclosed in EPO Application No. 85308547.0. These compounds, and their use as antiviral agents, are also disclosed in U.S. Pat. Nos. 4,526,988 and 4,692,434.

The present invention provides a new process for the inversion of 2-deoxy-2,2-difluororibose analogs to 2-deoxy-2,2-difluoroxylose analogs useful as intermediates for the synthesis of 3'-substituted-2',2'-difluoronucleosides for use as both oncolytic and antiviral agents. Novel intermediates used for this inversion are also provided.

SUMMARY OF THE INVENTION

The present invention provides a process for preparing a 2-deoxy-2,2-difluoroxylose of the formula

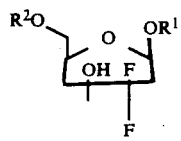

wherein $R^1$ and $R^2$ are independently hydroxy protecting groups; comprising the oxidation of a ribose of the formula

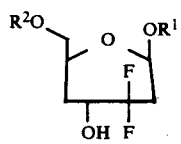

in the presence of an inert organic solvent, to prepare an intermediate of the formula

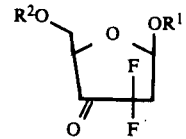

followed by the stereoselective reduction with a hydride reducing agent of the compound of Formula III in an inert solvent to give the xylose of Formula I.

The present invention further provides an intermediate of the formula

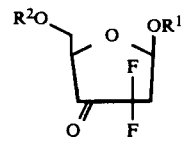

wherein $R^1$ and $R^2$ are independently hydroxy protecting groups.

DETAILED DESCRIPTION OF THE INVENTION

The term "hydroxy protecting group" represents that substituent which can be placed efficiently on a hydroxy group, and which can be removed easily when the reaction is complete. Suitable groups may be those described in standard textbooks, such as Chapter 3 of *Protective Groups in Organic Chemistry*, McOmie, Ed., Plenum Press, New York (1973); and Chapter 2 of *Protective Groups in Organic Synthesis*, Greene, John Wiley and Sons, New York (1981). Suitable hydroxy protecting groups commonly employed include formyl,

2-chloroacetyl, benzyl, diphenylmethyl, triphenylmethyl, 4-nitrobenzyl, phenoxycarbonyl, $C_1$–$C_4$ alkyl such as t-butyl, methoxymethyl, tetrahydropyranyl, allyl, tetrahydrothienyl, 2-methoxyethoxymethyl, methoxyacetyl, phenoxyacetyl, isobutyryl, ethoxycarbonyl, benzyloxycarbonyl, and optionally substituted benzoyl. The term "optionally substituted benzoyl" represents a benzoyl group with 0l–2 substituents on its benzene ring. These substituents commonly are independently halogen, nitro, cyano, $C_1$–$C_4$ alkoxy, benzyloxy or $C_1$–$C_4$ alkyl.

Silyl hydroxy-protecting groups are particularly convenient because most of them are cleaved easily by contact with water, an alcohol, or fluoride ion. They are of the general formula Si(R', R'', R''') where R', R'' and R''' are independently methyl, ethyl, propyl, isopropyl, butyl, isobutyl, sec-butyl, t-butyl or phenyl. Such groups may include trimethylsilyl, isopropyldimethylsilyl, methyldiisopropylsilyl, t-butyldimethylsilyl, diphenylmethylsilyl, triisopropylsilyl and the like.

All compounds of Formula III are useful but certain compounds are preferred and are described by the following limitations. It will be understood that further preferred subclasses of intermediates are to be obtained by combining the following limitations.

(a.) $R^1 \neq R^2$;

(b.) $R^1$ is a silyl protecting group, especially t-butyldimethylsilyl;

(c.) $R^2$ is a hydroxy protecting group selected from $C_1$–$C_4$ acyl or especially optionally substituted benzoyl.

The compounds employed as starting materials in the process of this invention are readily synthesized by procedures taught in U.S. Pat. Nos. 4,526,988 and 4,692,434, herein incorporated by reference.

The process of this invention, wherein the configuration of the C-3 hydroxy of a 2-deoxy-2,2-difluororibose is inverted by an oxidation/reduction sequence to the corresponding xylose, is represented by the following scheme:

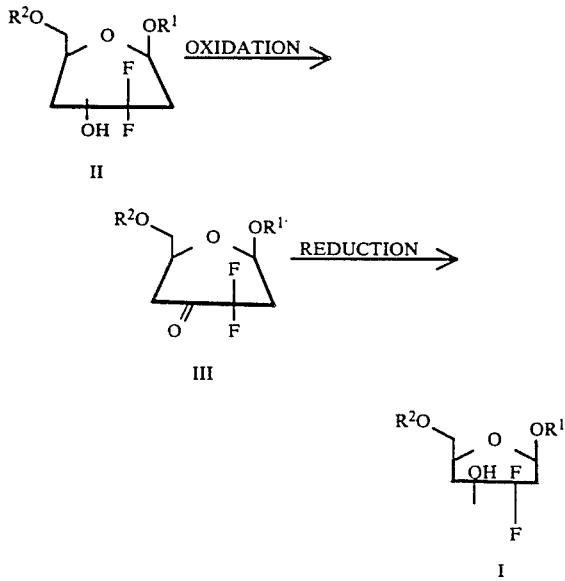

wherein $R^1$ and $R^2$ are as previously defined.

In the oxidation step of the process the starting ribose in an inert solvent is added to a solution or suspension of an appropriate oxidizing agent. The reaction mixture is then stirred until all starting material has reacted, usually from about 15 minutes to about 3 hours, at a temperature ranging from 0° C. to about 50° C. The product is isolated by filtration through a pad of silica gel or Florisil (Fisher). The filter pad is eluted with several volumes of a solvent such as ethyl acetate or diethyl ether to remove any product absorbed on the filter pad. The combined filtrates are concentrated under reduced pressure to give the 3-oxo-2-deoxy-2,2-difluorocarbohydrate intermediate which can be used without further purification.

Any number of oxidizing agents are generally useful for this reaction, such as ruthenium tetroxide, dimethyl sulfoxide with dicyclohexylcarbodiimide, dimethyl sulfoxide with acetic anhydride, dimethyl sulfoxide with phosphorus pentoxide, activated manganese dioxide and chromium oxidizing agents. The chromium oxidizing agents, in the presence of acetic anhydride, are preferred and include but are not limited to chromium trioxide, chromium trioxide with pyridine, pyridinium dichromate, sodium or potassium dichromate in acetic acid, sodium or potassium dichromate in sulfuric acid, chromyl chloride, di-t-butyl chromate and especially pyridinium chlorochromate.

The solvent used for the oxidation depends upon the specific oxidant used and the solubility characteristics of the substrate to be oxidized. Preferred solvents include water, acetic acid, methylene chloride, chloroform and carbon tetrachloride. The solvents can be used separately or in combination. Methylene chloride is a preferred solvent when chromium oxidizing agents are used.

In the reduction step of the process the intermediate 3-oxo-2,2-deoxy-2,2-difluorocarbohydrate is dissolved in an inert solvent and the solution is cooled to about 0° C. To this solution is then added a slight excess, approximately 10%, of an appropriate hydride reducing agent. The reaction mixture is stirred at room temperature for from about 1 hour to about 4 hours, as required for complete conversion of starting material to product. The reaction mixture is then quenched by the addition of a lower alkanol, typically methanol, and is then washed with several aqueous solutions. The remaining organic phase is dried and then concentrated under reduced pressure to give the desired 2-deoxy-2,2-difluoroxylose which may be purified by $C_{18}$ reverse phase or silica gel chromatography if necessary.

Many hydride reducing agents are generally useful for this reaction such as lithium aluminum hydride; alkylaluminum compounds such as diisobutylaluminum hydride and lithium t-butyldiisobutyl aluminum hydride; sodium borohydride and derivatives such as zinc borohydride; sodium alkoxyborohydrides such as sodium hydridotri(sec-butoxy)borate; organoborane reagents such as potassium tri(sec-butyl)borohydride (K-selectride) and lithium triethylborohydride; and preferably alkoxyaluminum hydrides such as lithium trimethoxyaluminum hydride or especially lithium tri(t-butoxy)aluminum hydride.

The choice of solvent for the reduction step of the process is dependent upon the hydride reducing agent used and the solubility characteristics of the substrate to be reduced. When sodium borohydride is used as the reducing agent, for example, a lower alkanol such as ethanol is an acceptable solvent for the reaction. When an aluminum hydride derivative is used as reducing agent, however, an anhydrous ether such as tetrahydrofuran, diethyl ether or mixtures thereof are preferred solvents. When using the preferred reducing agent, lithium tri(t-butoxy)aluminum hydride, a solvent system consisting of diethyl ether containing 20% tetrahydrofuran is optimal.

The 3-xylocarbohydrates of Formula I available by the process of this invention are useful as intermediates to 3'-substituted-2', 3'-dideoxy-2',2'-difluoronucleosides. The hydroxy substituent at the 3-position of a difluoroxylose of Formula I is functionalized with a trifluoromethanesulfonyl substituent. The resulting intermediate is treated with an azide reagent to give the corresponding 3-azido-2,3-dideoxy-2,2-difluororibose. This intermediate may then be catalytically hydrogenated to give the corresponding 3-amino-2,3-dideoxy-2,2-difluororibose. This reaction is represented by the following scheme.

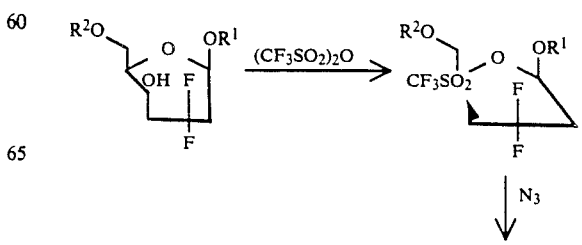

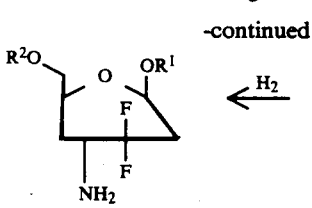 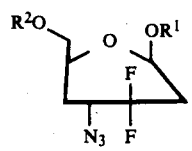

The reaction of a xylose of Formula I with the trifluoromethanesulfonyl reagent is carried out according to standard acylation conditions. The trifluoromethanesulfonyl reagent will contain a halogen substituent, with trifluoromethanesulfonyl chloride being preferred, or will be trifluoromethanesulfonic anhydride which is the especially preferred reagent. Typically an excess of such reagent is combined with a solution of the starting material dissolved in a mutual organic solvent. This reaction is complete within about 12 to 24 hours and it is generally conducted at a temperature from about 20° C. to about 100° C. The desired product may be isolated by standard techniques.

The 3'-trifluoromethanesulfonyloxy derivative thus prepared is next reacted with an equimolar to excess amount of an azide reagent for conversion to the appropriate 3'-azido derivative. Typical azide reagents include trimethylsilyl azide as well as the alkali metal azides such as lithium azide, sodium azide or potassium azide. The reaction is carried out in a suitable solvent under anhydrous conditions at a temperature in the range of about 100° C. to about −100° C. Suitable solvents include the aprotic solvents with N,N-dimethylformamide being preferred. The resulting compound may be converted to the 3-amino derivative under standard catalytic hydrogenation procedures if desired.

The nucleosides may now be prepared by attaching the appropriately substituted carbohydrate to the desired base according to standard procedures. The protecting group at the 1-position of the carbohydrate must be removed first. Most silyl protecting groups are easily cleaved by contact with water or an alcohol. The t-butyldimethylsilyl group requires acid conditions, such as contact with gaseous hydrogen halide or aqueous trifluoroacetic acid, for its removal. An appropriate leaving group must now be placed at the 1-position of the carbohydrate in order to obtain efficient reaction with the base. The preferred leaving group is methanesulfonyl, which is readily provided by reaction with methanesulfonyl chloride in the presence of a suitable acid scavenger such as triethylamine and the like. Other sulfonyl leaving groups, particularly toluenesulfonyl, are provided in the same way by reaction with the appropriate sulfonyl halide.

When a chloro or bromo leaving group is to be used, it is frequently convenient to first make the 1-acetate derivative, for instance by reaction with acetic anhydride, or another source of acetyl groups, in the presence of an equivalent or more of an acid scavenger. Then the acetate group is displaced with gaseous hydrogen bromide or hydrogen chloride, at a low temperature such as about −50° C. to about 0° C. Since the gaseous hydrogen halide may tend to remove the protecting groups, especially silyl protecting groups, it is necessary to operate this step at quite a low temperature and to add the hydrogen halide slowly in small increments.

The bases used to form the compounds of the present invention are commonly known to organic chemists, and no discussion of their synthesis is necessary. However, the primary amino groups which are present on some of the bases and sugars should be protected before the base is coupled with the carbohydrate. The usual amino-protecting groups are used, including silyl groups such as have been discussed, as well as such typical groups as t-butoxycarbonyl, benzyloxycarbonyl, 4-methoxybenzyloxycarbonyl, 4-nitrobenzyloxycarbonyl, formyl, acetyl, and the like.

It is often advisable to convert keto oxygen atoms on the bases to the enol form, in order to make the bases more highly aromatic and thereby allow more ready attack of the base by the carbohydrate. It is most convenient to enolize the oxygens by providing silyl protecting groups for them. The usual silyl protecting groups as discussed above are used for this purpose, also.

The reaction between the protected carbohydrate and the base is preferably carried out neat at an elevated temperature in the range of from about 50° C. to about 200° C. It is possible, however, to use relatively high-boiling solvents for the reaction, such as dimethylformamide, dimethylacetamide, hexamethylphosphoramide and the like. However, if the coupling reaction is carried out under elevated pressure, to avoid distillation of a low-boiling solvent, any convenient inert reaction solvent can be used.

The coupling reaction may be done at low temperatures if a reaction initiator, such as a trifluoromethanesulfonyloxysilane, is used. The usual inert reaction solvents, as discussed above, may be used at temperatures in the range of from about ambient to about 100° C.

The protecting groups may now be removed to provide the 3'-substituted-2',3'-dideoxy-2',2'-difluoronucleosides. The silyl protecting groups may be removed as described above.

Acyl protecting groups are removed by simple hydrolysis with strong or moderately strong bases, such as alkali metal hydroxides, at temperatures from about the ambient temperature to about 100° C. At least one equivalent of base is needed for each protecting group, of course. Such hydrolyses are conveniently carried out in hydroxylic solvents, especially aqueous alkanols. The reactions may be also carried out, however, in any convenient solvent, such as polyols including ethylene glycol, ethers such as tetrahydrofuran and the like, ketones such as acetone and methyl ethyl ketone and other polar solvents such as dimethylsulfoxide. The cleavage of acyl protecting groups may also be performed with other bases, including, for example, sodium methoxide, potassium t-butoxide, hydrazine, hydroxylamine, ammonia, alkali metal amides and secondary amines such as diethylamine and the like. The acyl protecting groups can also be removed with acid catalysts, such as methanesulfonic acid, hydrochloric acid, hydrobromic acid, sulfuric acid, or with acidic ion exchange resins. It is preferred to carry out such hydrolyses at a relatively high temperature, such as the reflux temperature of the mixture, but temperature as low as ambient may be used when particularly strong acids are used.

The following examples further explain the process of this invention.

EXAMPLE I

α and β-1-(t-butyldimethylsilyloxy)-3-oxo-5-benzoyl-2-deoxy-2,2-difluororibose.

(a.) To a solution of 1.0 gm (10.4 mMol) chromium trioxide in dichloromethane (100 mL) were added 1.6 mL (20.8 mMol) pyridine and the deep red solution was stirred for 15 minutes at room temperature. To this was then added a solution of 1.0 gm (2.6 mMol) α and β-1-(t-butyldimethylsilyloxy)-5-benzoyl-2-deoxy-2,2-difluororibose in dichloromethane (15 mL) dropwise followed by the addition of 1.0 mL (10.4 mMol) acetic anhydride. The reaction mixture was then stirred for 1 hour at room temperature. The reaction mixture was filtered through a pad of silica gel which was eluted with ethyl acetate (300 mL). The combined filtrates were concentrated in vacuo to give 0.88 gm (88%) of the desired product as a colorless oil. FD-MS: m/e=329 (m-57, loss of t-butyl group).

(b.) A solution of 50 mg (0.13 mMol) α and β-1-(t-butyldimethysilyloxy)-5-benzoyl-2-deoxy-2,2-difluororibose in dichloromethane were added dropwise to a solution of 98 mg (0.26 mMol) pyridinium dichromate and 0.07 mL (0.77 mMol) acetic anhydride in dichloromethane (6 mL). The resulting mixture was stirred at reflux for 2½ hours. The reaction mixture was cooled to room temperature, diluted with diethyl ether and filtered through a pad of silica gel. The pad was eluted further with diethyl ether and the combined filtrates were concentrated in vacuo to give 25.2 mg (50%) of the desired product as a colorless oil. FD-MS: m/e=329 (M-57, loss of t-butyl).

EXAMPLE II

β-1-(t-butyldimethylsilyloxy)-3-oxo-5-benzoyl-2-deoxy-2,2-difluororibose.

To a slurry of 6.0 gm (27.8 mMol) pyridinium chlorochromate in dichloromethane (200 mL) were added 13.1 mL (138.8 mMol) acetic anhydride followed by a solution of 7.2 gm (18.5 mMol) β-1-(t-butyldimethylsilyloxy)-5-benzoyl-2-deoxy-2,2-difluororibose in dichloromethane (200 mL). The reaction mixture was stirred at reflux for 2 hours. The resulting mixture was cooled to room temperature, diluted with diethyl ether and filtered twice through Florisil (Fisher) pads. The combined filtrates were concentrated in vacuo to give 6.9 gm (96%) of the desired product as a light yellow oil. FD-MS: m/e=329 (M-57, loss of t-butyl). IR(neat): 1800.5 cm$^{-1}$ (C=O) $^1$H-NMR (300 MHz, CDCl$_3$): δ 8.06 (m, 2H), 7.59 (t, 1H), 7.46 (t, 2H), 5.43 (d, 1H, J=7.9 Hz), 4.65 (m, 2H), 4.50 (m, 1H), 0.91 (s, 9H), 0.17 (d, 6H).

EXAMPLE III

α and β-1-(t-butyldimethylsilyloxy)-5-benzoyl-2-deoxy-2,2-difluoroxylose/ribose.

To a solution of 57 mg (0.15 mMol) α and β-1-(t-butyldimethylsilyloxy)-3-oxo-5-benzoyl-2-deoxy-2,2difluororibose in a mixture of diethyl ether (8 mL) and tetrahydrofuran (2 ml) at 0° C. were added 41 mg (0.16 mmol) lithium tri-(t-butoxy)aluminum hydride and the reaction mixture was stirred 2 hours at room temperature. To this solution was then added methanol (1.0 mL) and the reaction mixture was washed sequentially with 1N hydrochloric acid, brine, saturated aqueous sodium bicarbonate and brine. The remaining organic phase was dried over sodium sulfate and concentrated in vacuo to give 40 mg (69%) of the alcohol as a colorless oil. HPLC analysis performed on a C$_{18}$a-reverse phase column eluting with 75% acetonitrile in water at a flow rate of 3 ml/min showed the product to be a 5:1 mixture of xylo:ribo isomers at the C-3 position. FD-MS: m/e=331 (M-57, loss of t-butyl).

Several other agents are useful for the reduction of the C-3 ketone, giving variable ratios of C-3 xylo:ribo alcohols. Table I summarizes the results of typical reactions.

TABLE I

| Example | Reducing Agent | Solvent | Temp | % Yield | Xylo:[e] Ribo |
|---------|----------------|---------|------|---------|---------------|
| IV | NaBH$_4$ | Ethanol | Ambient | 48% | 2:1 |
| V | Li(Et$_3$)BH | THF | Ambient | —[a] | 2:1 |
| VI | L-Selectride[b] | THF | −78° C. | 41% | 4:1 |
| VII | DIBAL[c] | THF | −70° C. | —[d] | 2.3:1 |
| VIII | Li(tBu)(iBu)$_2$AlH | THF | −78° C. | 57% | 3:1 |

[a]Unable to determine yield because of contamination of product with a triethylboron derivative.
[b]L-Selectride = Lithium tri(sec-butyl)borohydride.
[c]DIBAL = diisobutylaluminum hydride.
[d]Reaction mixture contained approximately 40% unreacted starting material.
[e]Ratio of xylo to ribo isomers at the C-3 alcohol as determined by HPLC. HPLC analysis was performed on a reverse phase column eluting with a solution of 75% acetonitrile in water at a flow rate of 3 mL/min.

EXAMPLE IX

β-1-(t-butyldimethylsilyloxy)-5-benzoyl-2-deoxy-2,2-difluoroxylose.

To a solution of 320.4 mg (0.83 mMol) β-1-(t-butyldimethylsilyloxy)-3-oxo-5-benzoyl-2-deoxy-2,2-difluororibose in diethyl ether (45 mL) and tetrahydrofuran (12 mL) at 0° C. were added 231 mg (0.91 mMol) lithium tri(t-butoxy)aluminum hydride and the reaction mixture was stirred for 3 hours at room temperature. The mixture was then quenched with methanol (1 mL) and washed successively with 1N hydrochloric acid, brine, saturated aqueous sodium bicarbonate and brine. The remaining organic phase was dried over sodium sulfate and concentrated in vacuo to give 255.2 mg (61%) of the desired compound as a colorless oil. FD-MS: m/e=389 (M+1), m/e=331 (M-57, loss of t-butyl). $^1$H-NMR (300 MHz, CDCl$_3$/D$_2$O): δ8.06 (m,2H), 7.59 (t, 1H), 7.46 (t, 2H), 5.21 (dd, 1H, J=6.6, 1.0 Hz), 4.69 (m, 1H), 4.54 (m, 2H), 4.26 (dd, 1H, J=9.8, 3.9 Hz), 0.94 (s, 9H), 0.20 (d, 6H, J=1.3 Hz).

The following examples demonstrate the use of a compound of Formula I of this invention as an intermediate to a 3'-substituted 2',3'-dideoxy-2',2'-difluoronucleoside.

EXAMPLE X 1-t-butyldimethylsilyloxy-5-benzoyl-3-trifluoromethanesulfonyloxy-2-deoxy-2,2-difluoroxylose.

To a solution of 2.3 gm (5.9 mMol) 1-t-butyldimethylsilyloxy-5-benzoyl-2-deoxy-2,2-difluoroxylose in dichloromethane (100 mL) were added 7.2 mL (88.5 mMol) pyridine and the reaction mixture was cooled to −20° C. To this was then added a solution of 1.5 mL (8.9 mMol) trifluoromethanesulfonic anhydride in dichloromethane (20 mL) dropwise at such a rate as to maintain the temperature between −5° and −20° C. The reaction mixture was stirred for 40 minutes at −15° C. The reaction mixture was then allowed to warm to room temperature and was washed with saturated aqueous sodium bicarbonate. The remaining organic layer was dried over magnesium sulfate and concentrated under reduced pressure to give 2.8 gm (90%) of the desired compound as a yellow oil. FD-MS: m/e=463(M-57, loss of t-butyl).

EXAMPLE XI 1-t-butyldimethylsilyloxy-5-benzoyl-3-azido-2,3-dideoxy2,2-difluororibose.

To a solution of 4.53 gm (8.7 mMol) 1-t-butyldimethyl-silyloxy-5-benzoyl-3-trifluoromethanesulfonyloxy-2-deoxy-2,2difluoroxylose in dimethylformamide (50 mL) were added 1.2 gm (25.2 mMol) lithium azide and the reaction mixture was heated at 70° C. for 40 minutes. The reaction mixture was then concentrated under reduced pressure and the residue dissolved in ethyl acetate. This solution was washed several times with saturated aqueous sodium chloride, dried over sodium sulfate and concentrated under reduced pressure. The residue was redissolved in a small amount of ethyl acetate and poured over a pad of silica gel, eluting with ethyl acetate. The filtrates were concentrated under reduced pressure to give 2.09 gm (58%) of the desired compound as a colorless oil. FD-MS: m/e=356, (M-57, loss of t-butyl), 357((M+1)-57, loss of t-butyl). IR(neat): 2114 cm$^{-1}$, N$_3$.

EXAMPLE XII

α and β-5-benzoyl-3-azido-2,3-dideoxy-2,2-difluororibose.

A solution of 1.0 gm (2.4 mMol) α-1-t-butyldimethyl-silyloxy-5-benzoyl-3-azido-2,3-dideoxy-2,2-difluororibose in 10 mL each of trifluoroacetic acid, water and tetrahydrofuran was heated at 65° C. for 3 hours. The volatiles were removed under reduced pressure to give the title compound as a brown oil in quantitative crude yield. The material was used without further purification. IR$^1$ 2115 cm$^{-1}$, N$_3$; 3400 cm$^{-1}$, OH FD-MS: m/e=300(M+1).

EXAMPLE XIII

α and β-1-mesyloxy-5-benzoyl-3-azido-2,3-dideoxy-2,2-difluororibose.

To a solution of 700 mg (2.34 mMol) α and β-5-benzoyl-3-azido-2,3-dideoxy-2,2-difluororibose in dichloromethane (10 mL) were added 0.4 mL (2.70 mMol) triethylamine and the reaction mixture was cooled to 5° C. To this were added 0.2 mL (2.58 mMol) methanesulfonyl chloride dropwise at such a rate that the temperature remained below 10° C. The reaction mixture was stirred for 2 hours at room temperature and was then quenched by the addition of cold 1N hydrochloric acid (6 mL). The organic layer was washed with water and the aqueous layers were reextracted with dichloromethane. The combined organic extracts were washed with saturated aqueous sodium chloride, dried over sodium sulfate and concentrated under reduced pressure to give the crude product as a brown oil. The product was purified by silica gel chromatography, eluting with hexane containing 0–25% ethyl acetate. 177 mg of pure β-anomer, 70 mg of pure α-anomer and 295 mg of a 2:1(α:β) mixture were recovered from different fractions of the chromatography to give a total yield of 542 mg (61%) of the title compounds. FAB-MS: m/e=378, 379(M+1, M+2), m/e=282(M-95, loss of methanesulfonyl). IR(neat): 2216 cm$^{-1}$, N$_3$.

EXAMPLE XIV

α and β-1'-(6-chloro-9H-purin-9-yl)-5'-benzoyl-2',3'-dideoxy-3'-azido-2',2'-difluororibose.

To a solution of 144 mg (0.93 mMol) 6-chloropurine, 244 mg (0.93 mMol) triphenylphosphine and 162 mg (0.93 mMol) diethylazodicarboxylate in tetrahydrofuran (5 mL) were added a solution of 278 mg (0.93 mMol) α and β-5-benzoyl-3-azido-2-deoxy-2,2-difluororibose in tetrahydrofuran (10 mL) dropwise and the reaction mixture was stirred for 18 hours at room temperature. Volatiles were removed under reduced pressure and the resulting brown oil was triturated with diethyl ether. The resulting suspension was filtered and the filtrate concentrated under reduced pressure to give 836 mg of a crude brown oil. Purification was accomplished by C$_{18}$ a-reverse phase chromatography, eluting with 55% acetonitrile in water. Fractions containing product were combined and concentrated under reduced pressure to give 110.9 mg (27%) of the title compounds as a colorless oil (α:β=1:1). The oil was dissolved in isopropanol and 25.3 mg of α-1'-(6-chloro-9H-purin-9-yl)-5'-benzoyl-3'-azido-2',3'-dideoxy-2', 2'-difluororibose were recovered as a colorless, crystalline solid. $^1$H-NMR(300 MHz, CDCl$_3$): δ8.82(d, 1H, J=small), 8.38(d, 1H, J=small), 8.15(d, 1H), 7.52(m, 4H), 6.63(t, 1H, J=9 Hz), 4.82(m, 1H), 4.70(m, 2H), 4.45(m, 1H).

EXAMPLE XV

α-1'-(6-amino-9H-purin-9-yl)-3'-azido-2',3'-dideoxy-2',2'-difluororibose.

A solution of 27 mg (0.062 mMol) α-1'-(6-chloro 9H-purin-9yl)-5'-benzoyl-3'-dideoxy-2',2'-difluororibose in isopropanol (12 mL) was placed in a steel bomb and the solution cooled to 0° C. Gaseous ammonia was bubbled into the reaction mixture for 5 minutes. The bomb was sealed and the reaction mixture heated at 80° C. for two days. The reaction mixture was cooled to room temperature and concentrated under reduced pressure. The residue was purified by reverse phase chromatography on a C$_{18}$ a column eluting with 15% acetonitrile in water at a flow rate of 9 mL/min. Fractions containing product were concentrated under reduced pressure to give 11.8 mg (61%) of the title compound as a colorless solid. FAB-MS: m/e=313(M+1), 315(M+3). IR$^1$ 2116 cm$^{-1}$, N$_3$. $^1$H-NMR(300 MHz, d$_7$-DMF): δ 8.41(d, 1H, J=2.4 Hz), 8.22(s, 1H), 7.47(s, br, 2H), 6.70(dd, 1H, J=11.5, 6.2 Hz), 5.01(m, 1H), 4.76(m, 1H), 3.85(m, 2H). $^{13}$C-NMR(300 MHz, d;-DMF): 157.30(C-6), 154.05(C-2), 150.49(C-4), 139.80(C-8), 123.65(C-2'), 119.43(C-5), 84.0(C-1'), 82.74(C-4'), 61.97(C-3'), 61.32(C-5').

EXAMPLE XVI

β-1'-(6-amino-9H-purin-9-yl)-3'-azido-2',3'-dideoxy-2',2'-difluororibose.

A solution of 47.2 mg (0.11 mMol) α and β-1'-(6-chloro-9H-purin-9-yl)-5'-benzoyl-3'-azido-2',3'-dideoxy-2',2'-difluororibose in isopropanol (15 mL) were treated as described in Example 16. Purification yielded 11.2 mg (33%) of the title compound as a colorless solid. FAB-MS: m/e=313(M+1). $^1$H-NMR(300 MHz, d$_7$-DMF): δ8.47(s, 1H), 8.23(s, 1H), 7.50(br. s, 2H), 6.51(dd, 1H, J=5.3, 4.9 Hz), 5.64(br. s, 1H), 5.21(m, 1H), 4.21(m, 1H), 3.92(m, 2H). $^{13}$C-NMR(300 MHz, d$_7$-DMF): 157.32(C-6), 153.90(C-2), 150.20(C-4), 139.65(C-8), 124.23(C-2'), 119.81(C-5), 84.21(C-1'), 80.50(C-4'), 60 91(C-3'), 60.80(C-5').

We claim:

1. A process for preparing a 2-deoxy-2,2-difluoroxylose of formula

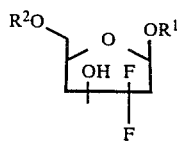

wherein $R^1$ and $R^2$ are independently hydroxy protecting groups; comprising the oxidation of a ribose of formula

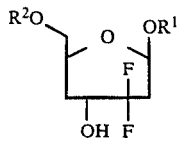

in the presence of an inert organic solvent to give an intermediate of formula

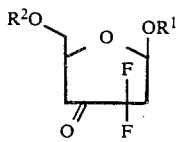

which is then reduced stereoselectively with a hydride reducing agent in an inert solvent.

2. A process of claim 1 wherein $R^1$ is a protecting group of formula Si(R', R'', R''') and R', R'' and R''' are independently methyl, ethyl, propyl, isopropyl, butyl, isobutyl, sec-butyl, t-butyl or phenyl.

3. A process of claim 2 wherein $R^1$ is t-butyldimethylsilyl.

4. A process of claim 2 wherein $R^2$ is $C_1$–$C_4$ acyl or optionally substituted benzoyl.

5. A process of claim 3 wherein $R^2$ is benzoyl.

6. A process of claim 1 wherein the oxidant is a chromium oxidizing agent in the presence of acetic anhydride.

7. A process of claim 6 wherein the chromium oxidizing agent is pyridinium chlorochromate.

8. A process of claim 1 wherein the hydride reducing agent is lithium tri-(t-butoxy) aluminum hydride.

9. A process of claim 4 wherein the reducing agent is lithium tri-(t-butoxy)aluminum hydride.

10. A process of claim 5 wherein the reducing agent is lithium tri-(t-butoxy)aluminum hydride.

11. An intermediate of formula

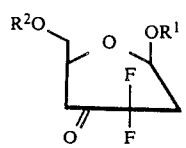

wherein $R^1$ and $R^2$ are independently hydroxy protecting groups.

12. An intermediate of claim 11 wherein $R^1$ is a protecting group of formula Si(R',R'',R''') and R', R'' and R''' are independently methyl, ethyl, propyl, isopropyl, butyl, isobutyl, sec-butyl, t-butyl or phenyl.

13. An intermediate of claim 12 wherein $R^1$ is t-butyldimethylsilyl.

14. An intermediate of claim 11 wherein $R^2$ is $C_1$–$C_4$ acyl or benzoyl substituted on its benzene ring with one or two substituents independently selected from halogen, nitro, cyano, $C_1$–$C_4$ alkoxy, benzyloxy or $C_1$–$C_4$ alkyl.

15. An intermediate of claim 12 wherein $R^2$ is $C_1$–$C_4$ acyl, benzoyl or benzoyl substituted on its benzene ring with one or two substituents independently selected from halogen, nitro, cyano, $C_1$–$C_4$ alkoxy, benzyloxy or $C_1$–$C_4$ alkyl.

16. An intermediate of claim 13 wherein $R^2$ is $C_1$–$C_4$ acyl, benzoyl or benzoyl substituted on its benzene ring with one or two substituents independently selected from halogen, nitro, cyano, $C_1$–$C_4$ alkoxy, benzyloxy or $C_1$–$C_4$ alkyl.

17. An intermediate of claim 15 wherein $R^2$ is benzoyl.

18. An intermediate of claim 16 wherein $R^2$ is benzoyl.

UNITED STATES PATENT AND TRADEMARK OFFICE
CERTIFICATE OF CORRECTION

PATENT NO. : 4,983,724
DATED : January 8, 1991
INVENTOR(S) : Larry W. Hertel et al.

It is certified that error appears in the above-identified patent and that said Letters Patent is hereby corrected as shown below:

Column 1, lines 47-54, delete the formula therein, and insert therefor

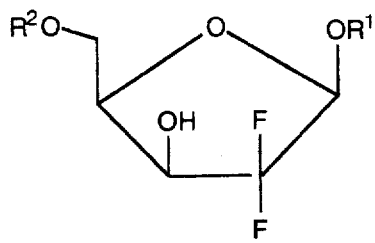

Column 1, lines 59-66, delete the formula therein, and insert therefor

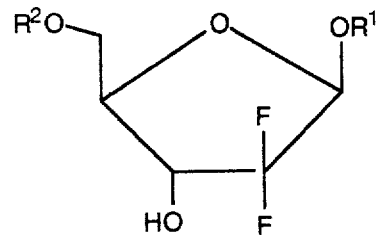

Column 2, lines 1-8, delete the formula therein, and insert therefor

UNITED STATES PATENT AND TRADEMARK OFFICE
CERTIFICATE OF CORRECTION

PATENT NO. : 4,983,724
DATED : January 8, 1991
INVENTOR(S) : Larry W. Hertel et al.

It is certified that error appears in the above-identified patent and that said Letters Patent is hereby corrected as shown below:

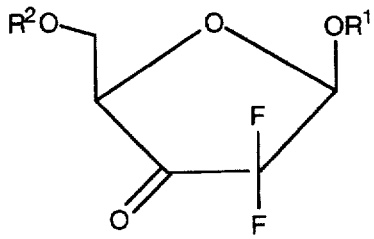

Column 2, lines 14-21, delete the formula therein, and insert therefor

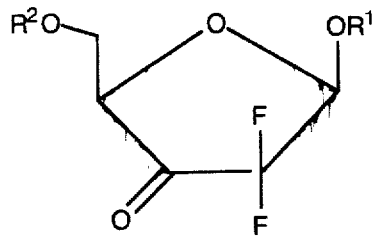

Column 3, lines 14-36, delete the reaction scheme therein, and insert therefor

UNITED STATES PATENT AND TRADEMARK OFFICE
CERTIFICATE OF CORRECTION

PATENT NO. : 4,983,724
DATED : January 8, 1991
INVENTOR(S) : Larry W. Hertel et al.

It is certified that error appears in the above-identified patent and that said Letters Patent is hereby corrected as shown below:

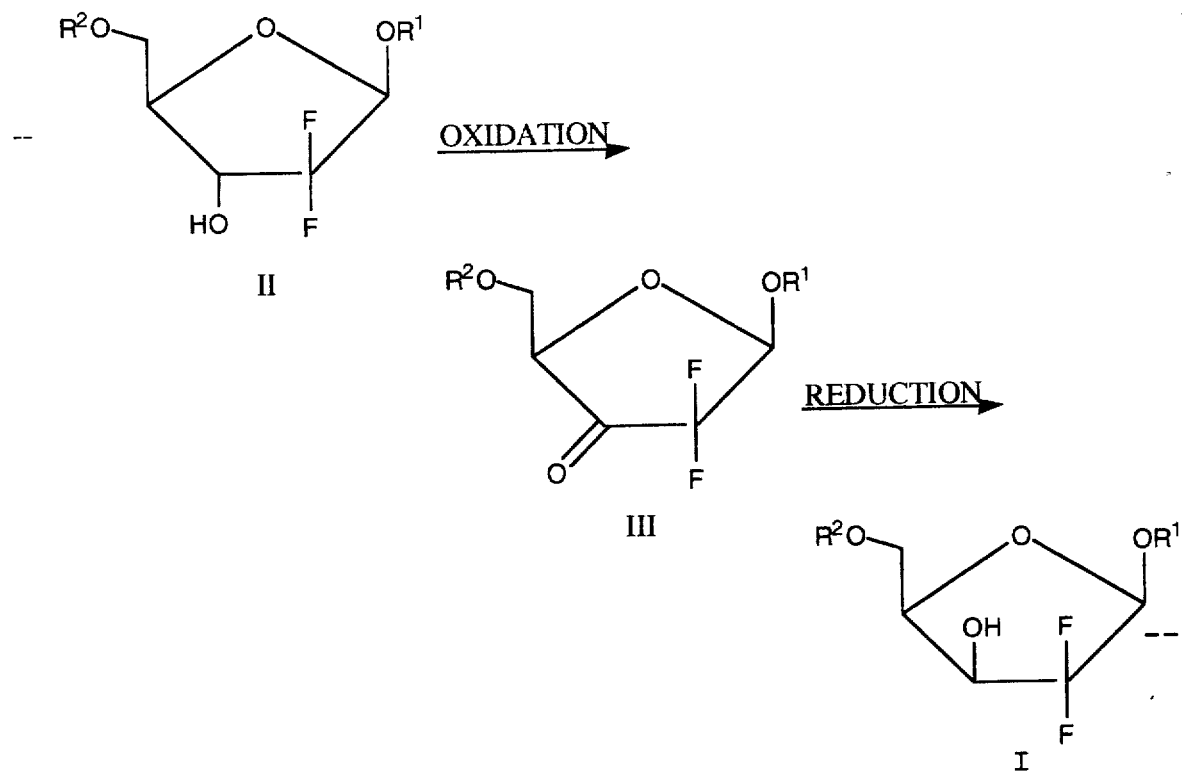

Column 4, line 59, to Column 5, line 9, delete the reaction scheme therein, and insert therefor

UNITED STATES PATENT AND TRADEMARK OFFICE
CERTIFICATE OF CORRECTION

PATENT NO. : 4,983,724
DATED : January 8, 1991
INVENTOR(S) : Larry W. Hertel et al.

It is certified that error appears in the above-identified patent and that said Letters Patent is hereby corrected as shown below:

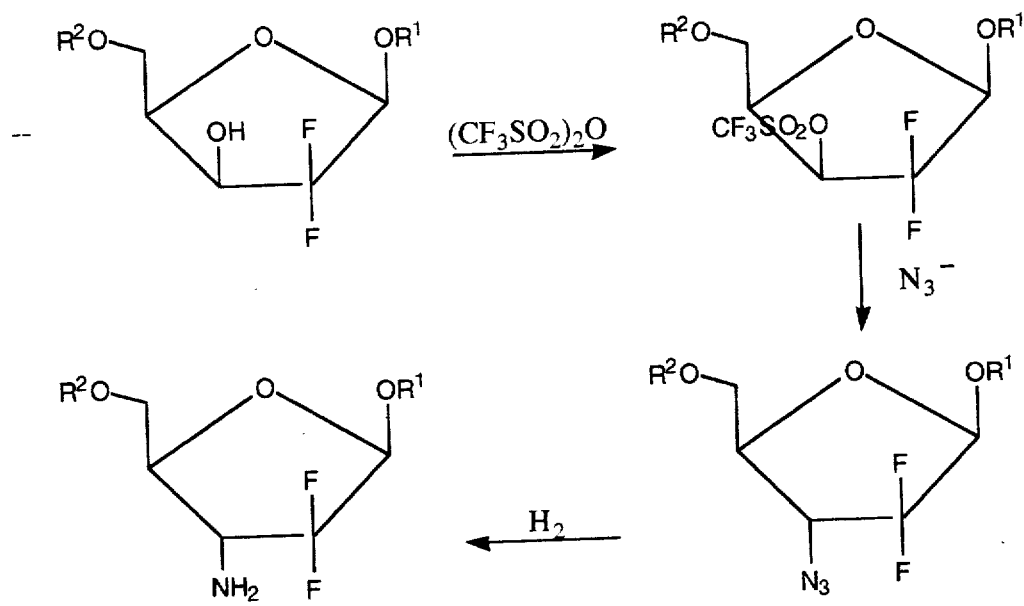

Claim 1, Column 11, lines 1-8, delete the formula therein, and insert therefor

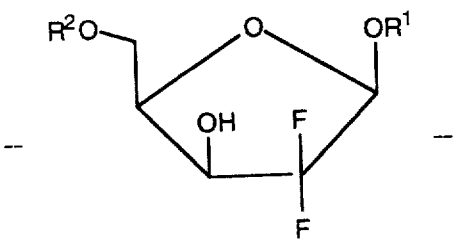

UNITED STATES PATENT AND TRADEMARK OFFICE
CERTIFICATE OF CORRECTION

PATENT NO. : 4,983,724

DATED : January 8, 1991

INVENTOR(S) : Larry W. Hertel et al.

It is certified that error appears in the above-identified patent and that said Letters Patent is hereby corrected as shown below:

Claim 1, Column 11, lines 12-19, delete the formula therein, and insert therefor

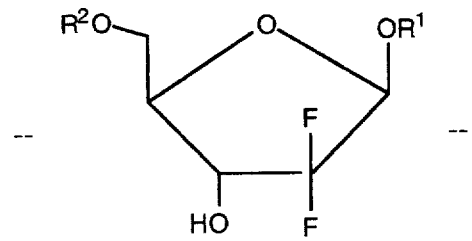

Claim 1, Column 11, lines 22-29, delete the formula therein, and insert therefor

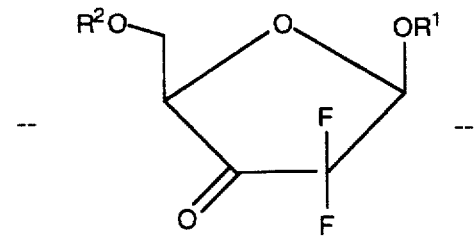

Claim 11, Column 12, lines 10-17, delete the formula therein, and insert therefor

UNITED STATES PATENT AND TRADEMARK OFFICE
CERTIFICATE OF CORRECTION

PATENT NO. : 4,983,724

DATED : January 8, 1991

INVENTOR(S) : Larry W. Hertel et al.

It is certified that error appears in the above-identified patent and that said Letters Patent is hereby corrected as shown below:

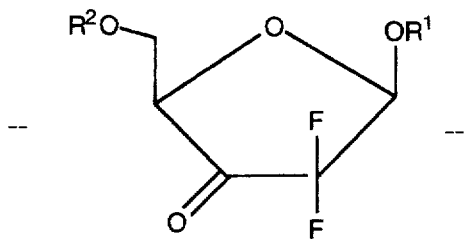

Claim 14, Column 12, line 27, after "acyl", insert --, benzoyl --.

Signed and Sealed this

Third Day of November, 1992

Attest:

DOUGLAS B. COMER

Attesting Officer

Acting Commissioner of Patents and Trademarks